United States Patent [19]
L'Orange

[11] 3,957,967
[45] May 18, 1976

[54] AGENT FOR THE CARE AND THE CLEANING OF TEETH AND DENTURES
[75] Inventor: Paul L'Orange, Mainz, Germany
[73] Assignee: Blendax-Werke R. Schneider & Co., Mainz, Germany
[22] Filed: July 1, 1974
[21] Appl. No.: 484,685

[30] Foreign Application Priority Data
July 27, 1973 Germany............................ 2338177

[52] U.S. Cl..................................... 424/48; 424/49; 424/54; 252/541
[51] Int. Cl.² ...................... A61K 7/22; A61K 7/30
[58] Field of Search .............................. 424/49–58; 252/152

[56] References Cited
UNITED STATES PATENTS

| | | | |
|---|---|---|---|
| 2,526,614 | 10/1950 | Butterfield............................ | 424/54 |
| 2,542,518 | 2/1951 | Henschol.............................. | 424/54 |
| 2,542,886 | 2/1951 | Wach..................................... | 424/54 |
| 2,549,759 | 4/1951 | Goodfriend........................... | 424/54 |
| 2,588,324 | 3/1952 | Lewis et al............................ | 424/54 |
| 2,588,992 | 3/1952 | Schlaeger.............................. | 424/54 |
| 2,601,238 | 6/1952 | Bell........................................ | 424/54 |
| 2,647,073 | 7/1953 | Singer.................................... | 424/54 |
| 3,728,446 | 4/1973 | Roberts et al. ....................... | 424/54 |
| 3,842,168 | 10/1974 | Colodney et al...................... | 424/52 |

OTHER PUBLICATIONS

Flotra et al. Siano, J. Dent. Res. 79(2): 119–112 (1971) "Side Effects of Chlorhexidine Mouth Washes".

Primary Examiner—Shep K. Rose
Attorney, Agent, or Firm—Connolly and Hutz

[57] ABSTRACT

Disclosed are compositions for the care and the cleaning of human teeth and dentures containing 1,6-di-4'-chlorophenyldiguanidohexane ("chlorhexidine") or the salts thereof and an amount of urea sufficient to reduce brown staining or discoloring of the teeth caused by the chlorohexidine. Also disclosed is a method of treating teeth and dentures comprising contacting them with urea and chlorohexidine.

10 Claims, No Drawings

AGENT FOR THE CARE AND THE CLEANING OF TEETH AND DENTURES

FIELD OF THE INVENTION AND STATE OF THE ART

The effectiveness of 1,6-di-4'-chlorophenyl-diguanidohexane, which is also known by the common name, chlorohexidine, or the salts thereof in preventing the occurrence of or in removing human dental plaque has been known for some time as described in numerous publications.

The practical utilization of this knowledge, i.e., the actual use of chlorohexidine in dental and oral care products, has been discouraged until now by the fact that even after a short application of chlorohexidine, a deep brown staining of the teeth and often also of the tongue occurs. It has already been proposed to prevent this staining by the use of water-insoluble salts of chlorohexidine (see, for example, German Published Pat. application No. 2,158,102). This proposal, however, could not be utilized to the extent that the salts exemplified in this German Published Application, such as the dihydrochloride, are water-soluble to a certain extent. Completely water-insoluble salts cannot have any effectiveness. In the use of these chlorohexidine salts, which are not water insoluble but soluble with difficulty, there also occurs the disturbing staining of the teeth and the tongue, even if to a lesser extent.

BRIEF SUMMARY OF THE INVENTION

It has now been found that the brown staining of teeth and tongue as well as of dentures which occurs when using chlorohexidine-containing dental care and cleaning compositions may be avoided if urea is added to such compositions. The preferred amount of urea employed is between about 0.5% and a maximum of about 45% of the total care and cleaning composition, and the precise amount used depends, inter alia, on the form of application of the dental care product. The preferred quantity range is between about 1.0 to 35% by weight of the total composition. The novel care and cleaning compositions of the present invention may be in the form of toothpastes, mouth washes, tooth powder, tooth cleaning tablets, chewing gum, chewing and sucking dragees, or also as gel-shaped, transparent toothpastes. In the event the compositions are intended for the cleaning of dentures, they may be employed preferably in the form of powder or tablets. The proportion of chlorohexidine or its salts in the compositions of this invention is between about 0.01 and 7.5% by weight of the total composition (calculated on free chlorohexidine).

DETAILED DESCRIPTION OF THE INVENTION

As already stated, aside from chlorhexidine, per se, its preferably water-soluble salts may also be employed in the novel preparations disclosed. These salts, in particular, include the digluconate and the diacetate of chlorhexidine; however, there may also be employed the dipropionate, the diformiate, the dilactate, the dihydrochloride, the dihydrofluoride, the dibromide, the sulfate, the phosphate, the succinate, the pivalate, the citrate, the tartrate, the maleate, the malate, the disarcosinate, the monofluorophosphate or the hexafluorophosphate of chlorohexidine. The active chlorohexidine agent thus may utilize any salt-forming radical provided, of course, that it is non-toxic under the application conditions employed.

If the novel dental care and cleaning composition is in the form of a toothpaste or a tooth powder, it customarily will contain polishing, binding, thickening and moisture-holding agents. In addition to calcium carbonate and the various calcium phosphates, the preferred polishing agent is particularly dicalcium phosphate or calcium pyrophosphate and in addition to the insoluble alkali methaphosphates, aluminum hydroxide may be used. Silicon dioxide is also well suited as a polishing agent in the novel dental care agents, particularly in particle sizes of 2 to 20 microns. Suitable polishing agents useful in the present invention are thus any of the well-known and conventional agents known for this purpose.

When silicon dioxide is used as a polishing agent, there may also be prepared, by the corresponding standardization of the glycerin content, a transparent, gel-shaped toothpaste, which optically is especially pleasing to the consumer.

In addition to polishing agents, toothpastes also contain binding, thickening, and moisture-holding agents and any of such well-known agents may be employed. Suitable binding and thickening agents are, for example, alkali salts of polyacrylic acid, cellulose derivatives such as hydroxy ethyl cellulose, Irish moss, tragacanth, and other mucilages.

As the moisture-holding agents or humectants, particularly glycerin and sorbitol as well as other sugar alcohols and various lower aliphatic diols have proven suitable.

The novel dental care and cleaning compositions of the present invention will also customarily contain preserving agents, preferably p-hydroxybenzoic acid ester as well as chlorphene bromide or even the 1,3-bis-($\beta$-ethylhexyl)-5-methyl-5-aminohexahydropyrimidine, known under the common name of Hexetidine.

The novel compositions furthermore may contain aromatic and flavoring agents. Saccharine sodium and sodium cyclamate, for example, may be used; the number of aromatic substances employable and their mixtures are practically unlimited and so well known to the art that they do not require an enumeration in detail.

The dental care agents, particularly mouth wash and toothpaste, are often added surface-active substances, e.g., for producing a foam when used.

The surface-active agents or tensides employed in the novel compositions must, of course, be compatible with the chlorohexidine or its salts. Such substances are, for example, higher alkyl sulfates and the salts thereof, e.g., sodium lauryl sulfate, salts of higher aliphatic acylamides of lower aliphatic amino acids, e.g., L-lauroylsarcosinate, protein fatty acid condensates in quantities of preferably not more than about 2.5% by weight, nonionic tensides, e.g., betaines, sulfobetaines or long-chain alkylamino carboxylic acids as well as cationic tensides, particularly quaternary ammonium compounds such as cetyltrimethylammonium bromide or diisobutylphenoxy ethoxyethyldimethylbenzylammonium chloride.

The novel dental care and dental cleaning compositions may also contain other substances known per se in dental and oral care agents besides chlorohexidine or the salts thereof, urea and the above-described customary agents and additives. Such substances, in particular, include the numerous fluorine compounds well known for the prevention of cavities such as sodium fluoride, potassium fluoride, alkali monofluorophosphate, stannous fluoride, manganese fluoride, long-chain aminofluoride, ethanolaminohydrofluoride, etc.

Also possible is the co-use of enzymes assisting the cleaning of teeth and the elimination of dental plaque, e.g., Dextranase or "Mutanase", complex formers for calcium and magnesium, vitamins, inorganic and organic phosphates, allantoin, β-pyridylcarbinole or glycyrrhetinic acid and the derivatives thereof.

In the event the novel composition comprises a cleaning agent for dentures, it may contain, aside from chlorohexidine or its salts and urea, substances splitting off oxygen in the known manner, e.g., alkali persulfates and/or alkali perborates, complex formers, particularly water-soluble polyphosphates, e.g., sodiumtripolyphosphate, sodiumhexamethaphosphate or trisodiumphosphate or ethylene diaminotetracetic acid and, if necessary, surface-active, particularly cation-active and non-ionogenic tensides as well as enzymes.

The concentration of the chlorohexidine in pulverulent or tablet-shaped cleaning agents for dentures is about 0.5 to about 25% by weight of the total composition. Where the novel composition is used in the form of a solution, a paste or a gel, the preferred chlorohexidine concentration is 0.05 to about 5% by weight of the total composition. The preferred urea concentration here also is between about 0.5 to a maximum of about 45% by weight of the total composition.

Given below are some examples for a more detailed explanation of the invention it being understood that such examples are for illustration only and do not limit the invention. The values given refer to percent by weight unless otherwise stated.

EXAMPLE I
TOOTHPASTE

| Ingredients | Percent |
|---|---|
| hydroxyethylcellulose | 0.90 |
| glycerin, 86% | 10.00 |
| sorbitol, 70% | 10.00 |
| water | 25.80 |
| chlorohexidine digluconate solution, 20% | 4.50 |
| urea | 25.00 |
| dicalciumphosphate dihydrate | 20.00 |
| silicon dioxide, pyrogenic | 1.50 |
| methyl-p-hydroxybenzoate | 0.15 |
| aroma mixture | 1.00 |
| sodiumlaurylsulfate | 1.00 |
| saccharin sodium | 0.15 |
| | 100.00 |

EXAMPLE II
TRANSPARENT TOOTHPASTE

| Ingredients | Percent |
|---|---|
| hydroxyethylcellulose | 0.30 |
| ethyl-p-hydroxybenzoate | 0.15 |
| saccharin sodium | 0.05 |
| glycerin, 99.5% | 57.00 |
| water | 9.48 |
| aroma mixture | 1.10 |
| chlorohexidine digluconate solution, 20% | 3.00 |
| urea | 15.00 |
| silicic acid (average particle diameter 3-20 microns) | 12.50 |
| sodium fluoride | 0.22 |
| sodium lauryl sulfate | 1.20 |
| | 100.00 |

EXAMPLE III
MOUTH WASH, READY FOR USE

| Ingredients | Percent |
|---|---|
| ethanol, pure | 5.000 |
| emulsifier | 1.500 |
| aroma mixture | 1.200 |
| sodium cyclamate | 0.500 |
| water, desalted | 82.799 |
| chlorohexidine digluconate solution, 20% | 1.000 |
| urea | 8.000 |
| food coloring, red | 0.001 |
| | 100.00 |

EXAMPLE IV
TOOTH CLEANING POWDER

| Ingredients | Percent |
|---|---|
| dicalcium phosphate dihydrate | 54.0 |
| dicalcium phosphate dihydrate anhydride | 8.0 |
| silicon dioxide, pyrogenic | 2.5 |
| sodium monofluorophosphate | 0.8 |
| saccharin sodium | 0.2 |
| sodiumlauroyl sarcosinate | 2.5 |
| chlorohexidine hydrochloride (B.P.) | 0.5 |
| urea | 30.0 |
| aroma | 1.5 |
| | 100.0 |

EXAMPLE V
TOOTH CLEANING TABLET

| Ingredients | Percent |
|---|---|
| tragacanth | 1.5 |
| polyvinyl pyrrolidone | 0.3 |
| silicon dioxide, pyrogenic | 0.5 |
| dicalciumphosphate dihydrate | 70.0 |
| aluminum hydroxide | 15.0 |
| aroma mixture | 1.1 |
| polyethylene glycol 1000 | 1.3 |
| chlorohexidine hydrochloride (B.P.) | 0.2 |
| urea | 10.0 |
| saccharin sodium | 0.1 |
| | 100.0 |

EXAMPLE VI
CHEWING GUM

Introduced into a chewing gum base having a customary composition per 100 parts by weight of the total composition were 1 part chlorohexidine monofluorophosphate, 5 parts urea and 0.3 parts sodium fluoride, thoroughly mixed, rolled, and then strand cut into ready-to-use strips.

EXAMPLE VII
CLEANING TABLETS FOR DENTURES

| Ingredients | Percent |
|---|---|
| sodium perborate monohydrate | 35.0 |

-continued

| Ingredients | Percent |
| --- | --- |
| trisodium phosphate | 5.0 |
| sodium tripolyphosphate | 15.0 |
| Potassium monopersulfate | 8.0 |
| sodium lauryl sulfoacetate | 0.5 |
| silicon dioxide, pyrogenic | 1.5 |
| peppermint oil | 0.3 |
| polyvinyl pyrrolidone | 2.0 |
| polyethylene glycol, 4000 | 2.0 |
| tartaric acid | 4.0 |
| sodium hydrogen carbonate | 16.6 |
| chlorohexidine hydrochloride (B.P.) | 0.1 |
| urea | 10.0 |
| | 100.0 |

EXAMPLE VIII

CLEANING POWDER FOR DENTURES

| ingredients | Percent |
| --- | --- |
| sodium perborate monohydrate | 40.0 |
| potassium monopersulfate | 5.0 |
| potassium sodium tripolyphosphate | 22.0 |
| silicon dioxide, pyrogenic | 2.2 |
| chlorohexidine acetate (B.P.C.) | 0.5 |
| urea | 30.0 |
| peppermint oil | 0.3 |
| | 100.0 |

EXAMPLE IX

GEL-SHAPED CLEANING AGENTS FOR DENTURES

| Ingredients | Percent |
| --- | --- |
| methylcellulose | 0.8 |
| hydroxyethylcellulose | 0.4 |
| glycerin | 20.0 |
| sodium aluminum silicate | 1.0 |
| water | 46.0 |
| peppermint oil | 0.3 |
| ethanol | 0.2 |
| chlorohexidine gluconate solution, 20% | 4.5 |
| urea | 25.0 |
| saccharose monolaurate | 2.8 |
| | 100.0 |

The above examples disclose compositions containing both urea and chlorohexidine. However, in treating the teeth or dentures, the application need not be simultaneous. For example, it has been found that a particularly good effect against dental plaque may be achieved and consequently an excellent teeth cleaning and caring of human teeth when the teeth are treated first with an agent, a toothpaste for example, containing about 0.5 to about 45% by weight urea and preferably an anion-active tenside, e.g., sodium lauryl sulfate, and subsequently the teeth are brought into contact with an agent, a mouth wash, for example, containing about 0.01 to about 7.5% by weight 1,6-di-4'-chlorophenyldiguanidohexane. In this manner, the discoloring effect of chlorohexidine may also effectively be prevented.

What is claimed is:

1. A dental care composition comprising 1,6-di-4'-chlorophenyldiguanidohexane or the non-toxic salts thereof in an amount of between about 0.01 and about 25 percent by weight of the composition based on free 1,6-di-4'-chlorophenyldiguanidohexane and urea, the amount of urea being sufficient to reduce the tendency of the 1,6-di-4'-chlorophenyldiguanidohexane or salts thereof to cause discoloration of the teeth, tongue or dentures and in an amount of between about 5.0 and about 45 percent by weight of the composition.

2. The dental care composition according to claim 1 wherein the 1,6-di-4'-chlorophenyldiguanidohexane or salts thereof are present in an amount of between about 0.01 and about 7.5 percent by weight of the composition based on free 1,6-di-4'-chlorophenyldiguanidohexane.

3. The dental care composition according to claim 1 containing a non-toxic carrier substance selected from the group consisting of a polishing agent, a binding and thickening agent, a moisture-holding agent, a surface active agent and mixtures thereof.

4. The dental care composition according to claim 3 in the form of a paste, a powder, a transparent gel, an aqueous solution, an alcoholic solution, a tablet, a dragee or chewing gum.

5. The dental care composition according to claim 3 wherein the 1,6-di-4'-chlorophenyldiguanidohexane is present as its diacetate or digluconate salt.

6. The dental care composition according to claim 3 in the form of a cleaning agent for dentures.

7. The dental care composition according to claim 1 wherein the amount of 1,6-di-4'-chlorophenyldiguanidohexane or salts thereof is between about 0.5 and about 25 percent by weight of the composition based on free 1,6-di-4'-chlorophenyldiguanidohexane and the composition is in the form of a tablet or powder for use as a denture cleaning agent.

8. The dental care composition according to claim 1 wherein the 1,6-di-4'-chlorophenyldiguanidohexane or salts thereof is present in an amount of about 0.05 to about 5 percent by weight of the composition based on free 1,6-di-4'-chlorophenyldiguanidohexane and the composition is in the form of a solution, a paste or a gel for use as a denture cleaning agent.

9. A method for treating teeth comprising contacting the teeth with 1,6-di-4'-chlorophenyldiguanidohexane or the salts thereof in an amount sufficient to prevent or remove dental plaque and with a composition containing urea in an amount sufficient to reduce the tendency of the 1,6-di-4'-chlorophenyldiguanidohexane or salts thereof to cause discoloration of the teeth and in an amount of between about 5.0% and about 45% by weight of said composition.

10. The method according to claim 9 wherein the teeth are first treated with a composition containing about 5 to about 45 percent by weight of the composition of urea and an anionic surface active agent and subsequently the teeth are treated with a composition containing about 0.01 to about 7.5 percent by weight of the composition of 1,6-di-4'-chlorophenyldiguanidohexane or salts thereof based on free 1,6-di-4'-chlorophenyldiguanidohexane.

* * * * *